United States Patent [19]

Lübbers

[11] 4,306,877
[45] Dec. 22, 1981

[54] OPTICAL MEASUREMENT OF CONCENTRATION

[75] Inventor: Dietrich W. Lübbers, Dortmund, Fed. Rep. of Germany

[73] Assignee: Max-Planck-Gesellschaft zur Forderung der Wissenschaften e.V., Göttingen, Fed. Rep. of Germany

[21] Appl. No.: 59,680

[22] Filed: Jul. 23, 1979

[30] Foreign Application Priority Data

Jul. 29, 1978 [DE] Fed. Rep. of Germany ....... 2833356

[51] Int. Cl.³ .................. G01N 21/80; G01N 33/48
[52] U.S. Cl. ............................. 23/230 R; 23/230 B; 23/928; 128/633; 204/195 M; 356/39; 356/306; 422/68; 422/91
[58] Field of Search ............ 422/66, 68, 67, 91; 23/230 R, 230 B, 232 R, 928; 356/39, 306; 364/498; 204/195 M, 195 P; 128/633

[56] References Cited

U.S. PATENT DOCUMENTS

| | | | |
|---|---|---|---|
| 3,907,503 | 9/1975 | Betts | 422/67 |
| 3,918,910 | 11/1975 | Soya et al. | 422/67 X |
| 3,932,132 | 1/1976 | Hijikata | 422/67 X |
| 4,003,707 | 1/1977 | Lubbers et al. | 356/39 |

*Primary Examiner*—Ronald Serwin
*Attorney, Agent, or Firm*—Michael J. Striker

[57] ABSTRACT

The concentration of a substance of interest is measured by exposing a permeable-membrane face of an indicator chamber containing an indicator to the substance, monochromator radiation being incident upon the indicator through a transparent wall of the indicator chamber, the exiting radiation being received by a light-metering unit for ascertainment of the effect upon the indicator's absorbence of fluorescence of the substance of interest. The indicator substance is additionally exposed to a reference substance of known concentration which is permitted to engage the indicator substance by diffusion through such permeable membrane, in order that the indicator be calibrated.

19 Claims, 5 Drawing Figures

4,306,877

OPTICAL MEASUREMENT OF CONCENTRATION

BACKGROUND OF THE INVENTION

The present invention concerns methods and arrangements for the optical measurement of the concentration of a substance of interest by resort to light measurement utilizing a monochromator and a light-metering unit. With methods and arrangements of this type, an indicator is contained in an indicator chamber at least a part of which is bounded by a membrane permeable to the substance of interest, with at least a part of the indicator chamber furthermore being transmissive for radiation entering and exiting the indicator chamber. The permeable membrane is placed in contact with the substance of interest, and molecules or particles of the substance of interest diffuse into the indicator chamber. Radiation from the monochromator is directed into the indicator chamber, and the spectral response of the indicator therein to the monochromator radiation (i.e., a change of color or a fluorescent response) depends upon the concentration of the substance of interest.

Using arrangements and methods of the type in question, it is necessary to calibrate the indicators employed, when high-precision concentration measurements are called for. This may be quite difficult, especially inasmuch as the indicator within the indicator chamber is generally not accessible but instead blocked from access by the aforementioned permeable membrane.

The indicator-chamber structure, containing an indicator and bounded by the aforementioned permeable membrane and radiation-transmissive wall is referred to herein as an optode, a term used in previous patents involving such type of indicator-chamber structure, e.g., U.S. Pat. No. 4,003,707.

One way to calibrate such an optode is by performing a concentration measurement with respect to a comparison substance whose concentration is known in advance, e.g., using a comparison sample containing the substance of interest in a known concentration. However, there exist applications in which this would be problematic due to the remoteness of the optode from the sample of interest, for example as in the case of blood gas concentration measurements performed using a catheter inserted into a blood vessel.

SUMMARY OF THE INVENTION

Accordingly, it is a general object of the invention to greatly facilitate the calibration of such optodes.

In accordance with one embodiment of the invention, the optode is provided with a comparison or reference chamber which can accommodate a reference sample of known concentration, with both the reference substance of known concentration and the substance of interest whose concentration is to be measured both permeating into the indicator compartment of the optode, so that the signals or signal components respectively attributable to the reference sample and the sample of interest can be compared, in one or another way, for calibration purposes.

The advantage of such an approach is that it becomes possible to perform calibrations in a very short time, with little or no manipulative work, and even concurrently with actual measurement of the concentration of the substance of interest.

In one embodiment of the invention, the optode has, as usual, a permeable-membrane face through which the substance of interest diffuses into the indicator compartment. However, the opposite face of the optode, through which the monochromator radiation enters the indicator compartment and through which the fluorescent radiation emitted by the indicator or merely the radiation reflected by the indicator exits the indicator compartment, is likewise a permeable membrane exposed to a reference sample, the reference sample being optically transmissive for the radiation which enters through it into the indicator compartment and exits through it from the indicator compartment.

In another embodiment of the invention, the optode comprises two component optodes. One of the component optodes is provided with means exposing its permeable membrane to a reference or comparison sample. Monochromatic radiation is incident upon both component optodes, and the radiation emitted from both component optodes is measured to generate a signal dependent upon the difference in the spectral response of the indicator contained in the two component optodes.

Particularly for certain contexts of use, it is advantageous that the optode be exposed to the reference sample by provision of a reference compartment bounded by a permeable membrane of the optode, with the reference sample being passed through the reference compartment. For example, if the optode is at the end of a catheter inserted into a blood vessel, the reference sample can be transmitted to and from the remote end of the catheter, so that calibration of the indicator can be performed with the catheter in place. The use of such a technique also makes it possible to employ the optode to measure the concentration of the substance of interest on a null-method basis. Using that technique, the concentration of the reference sample is initially zero and the optode exposed only to the sample to be measured. Then the concentration of the reference sample is progressively increased, until the spectral response of the indicator becomes identical to that which it exhibited in response to the reference sample alone.

It is especially advantageous to use for the reference sample a carrier substance containing the substance of interest, i.e., containing a component the same as the substance whose concentration is to be measured but of known concentration. In that event the measurement signal derived from the radiation emitted from the optode is indicative of the relative values of the known concentration of the substance of interest and the unknown concentration of the substance of interest.

When the measurement signal is, as just stated, indicative of the relative values of the known and unknown concentrations of the substance of interest, the measurement signal can also be used as an actuating signal for a servo adjuster operative for automatically varying the value of the known concentration until it equals that of the unknown concentration.

Using such an approach it becomes possible to measure the concentration of the substance of interest by resort to familiar relationships applying to the mixing ratio of two substances.

When the reference substance is a gas, this can greatly simplify the work performed in practical respects, because then the substances employed are easily mixed and also readily removed from the reference compartment.

However, the use of calibrating liquids can also be advantageous in some respects, e.g., by introducing the possibility of temperature control via the calibrating liquid itself, and by virtue of the ease with which a calibrating liquid can be transmitted, e.g., along the length of a catheter to the optode at the end of the catheter.

In another embodiment of the invention, in which use is made of two component optodes as referred to earlier, use is made of a fiber-optic structure having two branches at its remote end and three branches at its proximate end. One of the three proximate-end branches receives light from the monochromator employed, and the constituent fibers of this proximate-end branch extend through the fiber-optic structure towards the remote end, half of them going to one remote-end branch and the other half of them going to the other remote-end branch. The two component optodes are each located at one of the remote-end branches and receive monochromator radiation in this way. The other two proximate-end branches of the fiber-optic structure each emits light onto a respective one of two light-metering units, all the fibers of one of these two proximate-end branches extending to only a respective one of the two remote-end branches, and all the fibers of the other of these two proximate-end branches extending to only the other one of the two remote-end branches; in this way, the light emitted from each of the two component optodes finds its way only to a respective one of the two light-metering units employed.

With that arrangement, it becomes possible to locate one remote-end branch at the sample of interest, e.g., inserted into a blood vessel by means of a catheter, but with the other remote-end branch located outside or remote from the sample, e.g., so as to minimize the number of components which need be introduced by such catheter.

Alternatively, however, it is also contemplated that the reference chamber be provided as the head of a light-conductive catheter, with the conduits for transmission of the reference sample to and from the reference chamber running alongside and being fixed to the light-conductive structure of the catheter. This makes for a very simple structure particularly easy to handle when working in low-access contexts. This structure can be made particularly simple when the conduits for the reference sample are made of polymerized polyvinylchloride, with the reference conduits being of one piece with the chamber containing the indicator.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
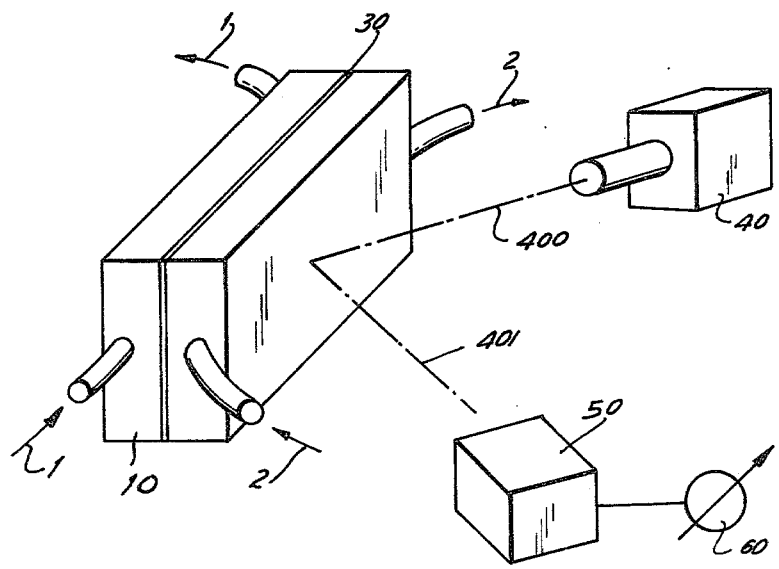
FIG. 1 depicts a set-up for the optical measurement of concentration, in which the optode employed is located between the sample of interest and a reference or comparison chamber.

In FIG. 1, a sample of interest 1, containing a substance of interest whose concentration is to be ascertained, is passed into and out of a measuring compartment 10. The right face of measuring compartment 10 is constituted by an optode 30. The use of optodes is disclosed, for example, in U.S. Pat. No. 4,003,707 granted Jan. 18, 1977. An optode is a compartment which contains an indicator substance. At least one wall of the optode is a membrane permeable to a substance of interest whose concentration in a sample of interest is to be measured. At least one wall of the optode, e.g., in the case of a planar optode the wall opposite to the permeable-membrane wall, is optically transmissive for monochromator radiation entering the indicator chamber of the optode, and likewise is optically transmissive for radiation exiting the optode; the exiting radiation may be fluorescent radiation emitted by an indicator which is excited by the monochromator radiation to an extent dependent upon the concentration of the molecules or particles of the substance of interest diffusing in through the permeable membrane, or the exiting radiation may be the reflected version of the monochromator radiation as reflected by an indicator whose spectral absorbance depends upon such concentration. As explained, for example, in the U.S. patent identified above, a planar optode may be essentially comprised of two layers, one being the permeable membrane, the other being the radiation-transmissive layer, with a layer of indicator confined therebetween. However, a planar optode may, for example, be so designed that both its opposite walls are permeable membranes themselves transmissive to the radiation in question.

In FIG. 1, the right face of optode 30 bounds a reference or comparison chamber 20 through which a reference sample is passed. The substance of interest in the sample of interest 1 diffuses through the left permeable-membrane wall of the optode 30 into the indicator space within the optode, and likewise, a reference substance passed through reference chamber 20 diffuses through the right permeable-membrane wall of optode 30 for interaction with the indicator within the optode. The reference substance in the reference sample 2 is of known concentration. The light 401 exiting from within the optode 30 passes through transparent reference compartment 20 and is received by a light-metering unit 50 provided with a numerical display 60. Initially the light measurement is performed with no reference sample present in reference chamber 20, so that the spectral (i.e., absorbance and/or fluorescence) response of the indicator within optode 30 be determined only by the concentration of the substance of interest in the sample of interest 1. Equivalently, if the reference sample 2 consists of an optically transparent carrier containing a substance which diffuses into optode 30, the concentration of the reference substance within the reference sample 2 can initially be kept at zero. The numerical value indicated by numerical display 60 is noted. Then, the concentration of the reference substance 2 transmitted through reference compartment 20 is progressively increased, until the numerical indication provided by display 60 is the same as before, i.e., the same as with no reference substance present. It is particularly advantageous that the reference substance 2, which diffuses into the right permeable-membrane wall of the optode 30 be identical, except in concentration, to the substance of interest in the sample of interest 1. In that case, when the reference concentration has been brought to a value resulting in a numerical read-out the same as before, there is simple correspondence between the known concentration of the reference substance and the now known concentration of the substance of interest in the sample of interest 1.

Figure 2:
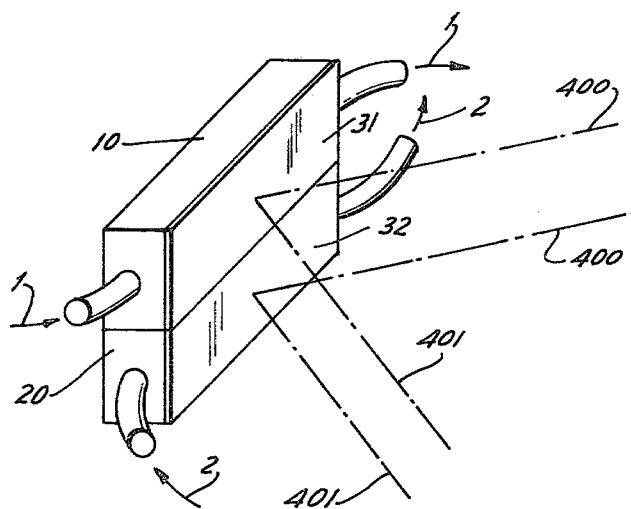
FIG. 2 depicts a structure making use of two component optodes.

FIG. 2 depicts another embodiment, in which the optode 30 employed consists of two component optodes 31, 32, for example formed by sealing-together the walls of optode 30 intermediate its upper and lower edges to form two separate internal indicator spaces. Monochromatic radiation 400 is incident as before, preferably from a single monochromator illuminating both component optodes 31, 32. In this embodiment, one component optode 31 is provided with the measuring chamber 10, and the other component optode 32 is provided with the reference chamber 20. The radiation 401 which exits from the two component optodes 31, 32 is preferably incident upon two light-metering units, each provided with a respective numerical display, such as 50, 60 in FIG. 1. When the concentration of the reference substance 2 has been brought to a value such that the metered radiation 401 exiting from both component optodes 31, 32 is the same, then the concentration of the substance of interest in the sample of interest 1 is now known to be equal to the reference concentration.

The configuration of FIG. 2 has the advantage that, by using component optodes 31, 32 of identical characteristics, the measurements become independent of fluctuations in the spectral composition of the radiation 400 employed.

Figure 3:
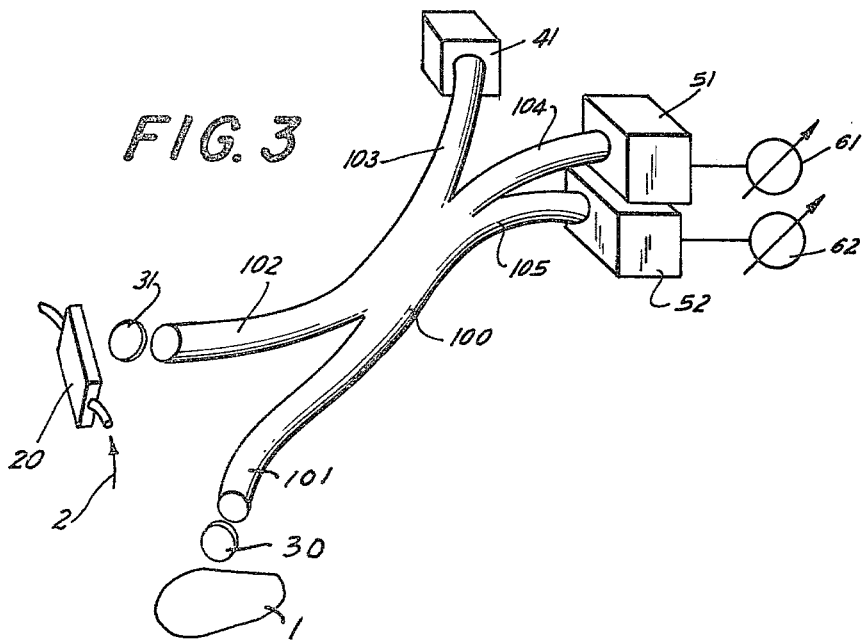
FIG. 3 depicts such a set-up utilizing a multi-branch fiber-optic structure, with an independently located auxiliary or reference optode.

FIG. 3 depicts a modification of FIG. 2, in which the two component optodes, the monochromator and the two light-metering units are optically intercoupled by means of a multi-branch fiber-optics structure 100. At its remote end, fiber-optics structure 100 has two branches 101, 102, and at its proximate end three branches 103, 104, 105. A monochromator 41 or other light source delivers light into branch 103. First and second component optodes 30, 31 are respectively located adjacent branches 101 and 102, and the two light-metering units 51, 52, with their respective numerical displays 61, 62 receive light from branches 104, 105. In particular, the constituent fibers of branch 103 extend, half of them, to branch 101, and the other half of them extend to branch 102. All the constituent fibers of branch 104 extend through to branch 101, and all the constituent fibers of branch 105 extend through to branch 102. Accordingly, the constituent fibers of branch 101 consist of fibers which discharge light from light source 41 and fibers which transmit light back to light-metering unit 51. Likewise, the constituent fibers of branch 102 consist of fibers which discharge light from light source 41 and fibers which transmit light back to light-metering unit 52. At the end face of each remote-end-branch 101 or 102, the light-emitting and light-receiving fibers can be randomly arranged or arranged in accordance with a predetermined spatial scheme.

The first component optode 30 is provided at the end of branch 101 and, here by way of illustration, is directly exposed to the sample of interest 1; alternatively, first component optode 30 could be provided with a respective measuring compartment as at 10 in FIG. 2. The second component optode 31 is provided at the end of branch 102 and is here provided with a respective reference compartment 20, i.e., as in FIG. 2.

With the configuration of FIG. 3, it becomes a simple matter to simultaneously irradiate both optodes 30, 31 and to simultaneously meter the light emitted from both. In FIG. 3, the various branches of fiber-optics structure 100 are shown quite spread apart, especially for the sake of clarity. The two branches 101, 102 can indeed be maintained spaced from each other, where the context of use makes this advantageous, for example where a low-access sample of interest 1 would make immediately adjoining location of the reference chamber 20 undesirable. Alternatively, however, the two branches 101, 102 can be understood to run directly alongside each other, with the two component optodes 30, 31 likewise located adjacent, e.g., with the two branches 101, 102 housed in a single tubular housing. Likewise, the three branches 103, 104, 105 might run alongside each other into a single housing containing the light source and the two metering units, or may be discrete branches such as shown. As before, when the numerical read-outs provided by the two displays 61, 62 are the same, then the reference concentration has been adjusted to equal the concentration to be ascertained.

In FIG. 3, as in all embodiments, it is not necessary to proceed on the basis of two measured-radiation signals and to bring them, in the manner explained above, into simple equality. For example, instead of two numerical displays, use may be made of a single numerical display operative for indicating the difference as between the two radiation measurements, with the operator then adjusting the reference concentration until the difference is reduced to zero. Alternatively, such difference signal may be used as the actuating signal for a servo regulator operative for automatically adjusting the reference concentration, so as to automatically bring the reference concentration into equality with the unknown concentration. In the case of the configuration disclosed in FIG. 1, the radiation-measurement signal produced by metering unit 50, accompanied by a signal indicating the concentration of the reference substance, could be applied to a computer, for determination of the unknown concentration by means of computation. These alternatives to progressive increase or decrease of the reference-substance concentration, having been stated, will be understood by persons skilled in the art.

Figure 4:
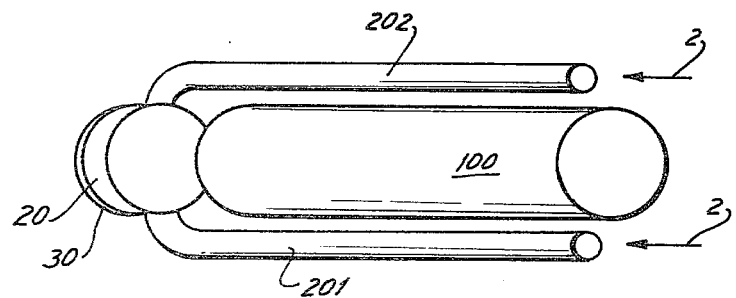
FIG. 4 depicts the remote end of a light-conductive catheter provided with an optode and a reference chamber.

FIG. 4 depicts a configuration contemplated for, but by no means limited to, a catheter-type use. Numeral 100 denotes a fiber-optics structure, only the end of which is shown, whose constituent fibers serve, some of them, for transmitting monochromator radiation to the optode 30 and, others of them, for transmitting reflected or fluorescent radiation back towards the light-metering unit employed. The proximate face of the optode 30 bounds a reference chamber 20 and the remote face of the optode is exposed to the sample of interest. Conduits 201, 202 transmit the reference sample to and from the reference compartment 20. For the sake of illustration, the conduits 201, 202 are shown spaced from the central fiber-optics structure 100, but these conduits would in practice be fastened to the fiber-optics structure along the length thereof.

Figure 5:
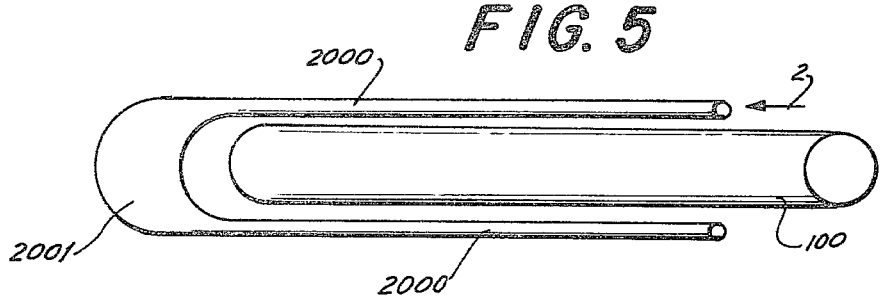
FIG. 5 depicts a reference-chamber construction formed from a tube through which a reference sample is passed, with the indicator of the optode being incorporated in the material of the tube.

FIG. 5 depicts a modification of the configuration depicted in FIG. 4. The optode and the reference chamber here are consolidated into a single unit, along with the conduits for the reference sample. Tubular structure 2000 comprises two conduit portions, corresponding to 201, 202 in FIG. 4. The remote end 2001 of this bent-around tubular structure is of enlarged size and constitutes the reference compartment for the reference substance. The tubular structure 2000 is made of polyvinylchloride, and the indicator substance employed is incorporated and sealed within the material of the wall of tubular structure 2000 at the region of the reference compartment 2001. Other materials suitable for the tubular structure 2000 would include, for example, agar or silicon. In this way, the interior surface of the reference compartment 2001 constitutes one face of the optode, exposed to the reference sample, whereas the exterior surface of reference compartment 2001 constitutes the opposite face of the optode, exposed to the sample of interest. The reference sample, at varied concentration, can be passed through reference compartment 2001, and alternately reference compartment 2001 can be emptied of the reference sample so as to obtain a measured-radiation signal dependent only upon the concentration of the substance of interest in the sample of interest, to which the exterior surface of reference compartment 2001 is exposed.

Configurations such as depicted in FIG. 5 can, it should be emphasized, also be used in cooperation with polarographic probes, and the like. For example, U.S. Pat. Nos. 3,918,434 and 3,985,633, both to Lübbers, et al., disclose a polarographic probe whose face is covered over by a permeable membrane, the membrane confining a layer of electrolyte between itself and the probe face across which it is stretched. In accordance with the present invention, a further membrane can be provided, covering over the electrolyte-bounding membrane of such probes, with the space internal to this double-membrane structure then constituting the reference compartment. Thus, the substance of interest whose concentration is to be polarographically ascertained diffuses into the electrolyte of the polarographic probe only after diffusing through the two membrane walls which define the reference compartment. Using the technique of FIG. 5, the membranes employed can be portions of the tubular structure used in FIG. 5, the reference compartment 2001 thereof being, however, pressed flatter for the sake of the configuration of such polarographic probes. If, then the polarographic probe is to be calibrated, a reference substance can be transmitted through the reference compartment, so that the reference substance diffuse through the permeable-membrane wall of the reference compartment into the electrolyte of the probe and cooperate with the polarographic electrodes of the probe. Of course, in such a context, the indicator substance incorporated and sealed within the material of the wall of the reference compartment 2001 of the tubular structure 2000 of FIG. 5 need not be provided for polarography purposes, and the substance whose concentration is to be polarographically ascertained merely enters from the sample of interest through the double-membrane reference compartment into the probe's electrolyte.

It will be understood that each of the elements described above, or two or more together, may also find a useful application in other types of set-ups and configurations differing from the types described above.

While the invention has been illustrated and described as embodied in conjunction with optodes and polarographic probes, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method for optically determining the concentration of a substance of interest, comprising, in combination, using an indicator substance confined in an indicator compartment at least a part of which is a membrane permeable to the substance of interest and at least a part of which is transmissive for light, using a monochromator to direct light onto the indicator substance through a transmissive part of the indicator compartment and using light-metering means to receive the light emitted from the indicator substance through a transmissive part of the indicator compartment, exposing a permeable-membrane part of the indicator compartment to a reference substance of known concentration and allowing the reference substance to diffuse into the indicator compartment, using the light-metering means to derive light-measurement signals dependent upon the concentration of the substance of interest and dependent upon the concentration of the reference substance of known concentration; and adjusting said signals to the same value by varying the known concentration of the reference substance.

2. The method defined in claim 1, the indicator compartment having a first side exposed to the substance of interest and a second side exposed to the reference substance, the reference substance being light-transmissive, with the monochromator light and the exiting light passing through the reference substance.

3. The method defined in claim 2, providing the indicator compartment with a reference compartment located alongside the indicator compartment and bounded by a permeable-membrane part of the indicator compartment, the reference compartment having an inlet and outlet, and transmitting a reference substance through the inlet and the outlet of the reference compartment.

4. The method defined in claim 2, the reference substance being the same substance as the substance of interest but being present in a known concentration in a carrier substance so as to constitute a reference sample to which the second side of the indicator compartment is exposed.

5. The method defined in claim 2, using the light-metering means to produce a signal simultaneously dependent upon both the unknown concentration of the substance of interest and the known concentration of the reference substance, by permitting both the substance of interest and the reference substance to simultaneously diffuse through a permeable-membrane part of the indicator compartment into the indicator substance therein.

6. The method defined in claim 2, using signals dependent upon the concentrations of the substance of interest and the reference substance to automatically vary the concentration of the reference substance.

7. The method defined in claim 4, the reference sample being gaseous.

8. The method defined in claim 4, the reference sample being a liquid.

9. A method for optically determining the concentration of a substance of interest, comprising, in combination, using two indicator compartments each containing an indicator substance, at least a part of each indicator compartment being a membrane respectively permeable to the substance of interest and a reference substance, at least a part of each indicator compartment being light transmissive, using a monochromator to direct light onto the indicator substance confined in the indicator compartments and using light-metering means to receive the light emitted from the indicator compartments, exposing a permeable-membrane part of one indicator compartment to the substance of interest and a permeable-membrane part of the other indicator compartment to a reference substance of known concentration, using light-metering means to derive light-measurement signals dependent upon the concentrations of the substance of interest and the reference substance, and adjusting said signals to the same value by varying the known concentration of the reference substance.

10. The method defined in claim 9, the reference substance being the same substance as the substance of interest but being present in a known concentration in a carrier substance so as to constitute a reference sample.

11. The method defined in claim 9, using the light-metering means to produce a signal dependent upon both the concentration of the substance of interest and the known concentration of the reference substance.

12. The method defined in claim 9, using signals dependent upon the concentrations of the substance of interest and the reference substance to automatically vary the concentration of the reference substance.

13. The method defined in claim 10, the reference sample being gaseous.

14. The method defined in claim 10, the reference sample being a liquid.

15. An optode system for use in optically determining the concentration of interest, the system comprising an indicator compartment accommodating an indicator substance and being constituted by two permeable membrane parts and being at least in part constituted by optically transparent material, a reference compartment bounded by one permeable-membrane part of the indicator compartment and having means for transmission of a reference substance through the reference compartment, so that the reference substance can diffuse through the one permeable-membrane part of the indicator compartment into the indicator substance, means for directing light through the optically transparent part, and light metering means to receive the light emitted from the indicator substance and to indicate a value corresponding to a measured concentration value.

16. In an apparatus for optical measurement of the concentration of a substance of interest, in combination, a fiber-optics structure having a first end comprised of respective first, second and third branches and a second end comprised of respective first and second branches, half the constituent fibers of the first branch of the first end extending through the fiber-optics structure to the first branch of the second end, with the other half of the constituent fibers of the first branch of the first end extending through to the second branch of the second end, all the constituent fibers of the second and third branches of the first end respectively extending through the fiber-optics structure to only the first branch of the second end and to only the second branch of the second end, first and second optodes located at respective ones of the first and second branches of the second end, a monochromator located at the first branch of the first end, and light metering means receiving light from the second and third branches of the first end of the fiber-optics structure.

17. An optode as defined in claim 15, furthermore including a catheter comprising a light-conductive structure, the optode being provided at the end of the catheter, the reference compartment being provided with conduits leading to and from the reference compartment and extending alongside the light-conductive structure fixedly fastened thereto.

18. An optode as defined in claim 17, the reference compartment and the conduits being part of a one-piece tubular element, an indicator substance being incorporated and sealed within the material of the tubular element.

19. An improved polarographic probe for measurement of the concentration of the substance of interest, the probe being of the type provided with reference and polarography electrodes terminating at a face of the probe with a permeable membrane covering over the face of the probe and confining between itself and the face of the probe a layer of electrolyte, the improvement comprising a permeable membrane covering the face of the probe and additionally defining a reference compartment having an inlet and an outlet through which a reference sample can be transmitted through the reference compartment.

* * * * *